United States Patent
Chao

Patent Number: 6,134,297
Date of Patent: *Oct. 17, 2000

[54] APPARATUS AND METHOD FOR REMOVING SCATTER FROM AN X-RAY IMAGE USING TWO-DIMENSIONAL DETECTORS AND A SINGLE-ENERGY SPECTRUM X-RAY SOURCE

[75] Inventor: Yong-Sheng Chao, Storrs, Conn.

[73] Assignee: Advanced Optical Technologies, Inc., E. Hartford, Conn.

[*] Notice: This patent is subject to a terminal disclaimer.

[21] Appl. No.: 09/207,635

[22] Filed: Dec. 9, 1998

[51] Int. Cl.[7] ...................................................... H05G 1/64
[52] U.S. Cl. ..................... 378/98.12; 378/98.4; 378/147
[58] Field of Search ................................. 378/98.2, 98.4, 378/98.7, 98.12, 147, 154

[56] References Cited

U.S. PATENT DOCUMENTS

| | | | |
|---|---|---|---|
| 5,327,476 | 7/1994 | Kemner | 378/98.4 |
| 5,648,997 | 7/1997 | Chao | 378/98.4 |
| 5,825,032 | 10/1998 | Nonaka et al. | 250/370.09 |

OTHER PUBLICATIONS

Joseph Y. Lo et al., Scatter Compensation in Digital Chest Radiography Using the Posterior Beam Stop Technique, 21 Medical Physics 435 (Mar. 1994).

Primary Examiner—David P. Porta
Attorney, Agent, or Firm—Morse, Altman & Martin

[57] ABSTRACT

An apparatus and method for removing scatter from x-ray images acquired by two-dimensional digital detectors. The apparatus consists of, in physical order, an x-ray source, a front two-dimensional x-ray detector, a beam selector, and a rear two-dimensional x-ray detector. The subject is located between the x-ray source and front detector. There two types of beam selectors, one allowing only primary x-rays to reach selected locations of the rear detector, and the other allowing primary x-rays and scatter to reach selected locations of the rear detector while allowing only scatter x-rays to reach shadowed locations of the rear detector. The method includes determining a low-resolution primary x-ray rear detector image, calculating an approximate low-resolution primary x-ray front detector image, calculating a high-resolution primary image at the front detector, and applying one or more of several correction procedures for achieving higher accuracy from the approximations.

14 Claims, 4 Drawing Sheets

APPARATUS AND METHOD FOR REMOVING SCATTER FROM AN X-RAY IMAGE USING TWO-DIMENSIONAL DETECTORS AND A SINGLE-ENERGY SPECTRUM X-RAY SOURCE

BACKGROUND OF THE INVENTION

1. Field of the Invention

The present invention relates generally to digital x-ray imaging and, more particularly, relates to methods and apparatuses for removal of scatter using two-dimensional, single-energy x-ray imaging.

2. The Prior Art

Reducing scatter is one of the best ways to improve image quality in x-ray imaging. For most imaging systems using two-dimensional detectors for human body imaging, the ratio of scatter to the primary signal is generally as high as between 50% and 100%. Randomly scattered x-rays tend to reduce image contrast, produce blurring, and reduce signal-to-noise ratio. Currently, clinical x-ray imaging uses the traditional Bucky grid for relieving adverse scatter effects. However, the Bucky grid is a rather inefficient and crude device. Even with the best grid design, the Bucky grid can only reduce the scatter to 30% or 20% of its total intensity, with a price being an increase in the patient's x-ray exposure by two to four times. Moreover, the Bucky grid was invented 90 years ago, largely designed for use with x-ray films, when only qualitative analog imaging was performed. No quantitative requirement existed. Recently, with the development of highly sophisticated large format integrated semiconductor x-ray detector arrays, an essentially new method for eliminating scatter interference in digital x-ray imaging is needed.

U.S. Pat. Nos. 5,649,997 and 5,771,269, and the disclosure of U.S. patent application Ser. No. 09/025,926 provide a rigorous scientific solution to the scatter problem. By using a dual-energy method, scatter can be essentially eliminated from x-ray images with a high accuracy that is limited only by that of the experimental data.

SUMMARY OF THE INVENTION

An object of the present invention is to provide a simplified solution to that disclosed in the above-identified U.S. patents and application. In certain cases, when the required accuracy for removal of scatter is not very high, for example, in the range between 5% to 10% or sometimes larger, the dual-energy method can be replaced by a single-energy method using an x-ray source with a single-energy spectrum output. The most important advantage of the present invention over the Bucky grid is that, without increasing the patient's exposure, the amount of scatter that can be removed is many times greater than that of the Bucky grid. Moreover, the Bucky grid tends to distort image data, which is highly undesirable in digital quantitative imaging. The present invention can maintain the original image data.

A typical application of the present invention is to use the detector structure and the scatter-removal method to replace the currently used x-ray film cassettes without replacing the existing x-ray source. In the present trend of technology upgrading from films-based x-ray imaging to direct digital imaging, many hospitals want to continue to utilize existing facilities whenever possible. The present invention can well meet these needs. When accurate quantitative imaging is not critical, the hospital only needs to purchase a digital detector system as described in the present invention to retrofit an existing single-energy x-ray source. Only the x-ray film cassettes and the Bucky grid are made obsolete.

The present invention comprises an apparatus and method for obtaining two-dimensional x-ray images with scatter interference approximately removed. The two embodiments of the apparatus of the present invention are described in detail in U.S. Pat. Nos. 5,649,997 and 5,771,269 and in U.S. patent application Ser. No. 09/025,926, all of which are incorporated herein by reference. There are two differences between the incorporated disclosures and the present apparatus. The first is that the x-ray source of the patents emits x-rays of two different energy spectrums, whereas in the present invention, the x-ray source emits x-rays of only a single-energy spectrum. The second difference is that, in several embodiments of the disclosures, the x-ray detectors are capable of distinguishing different x-ray energy levels, whereas in the present invention, this capability is not necessary.

Briefly, the apparatus includes, in physical sequence from front to back, an x-ray source, a front two-dimensional x-ray detector, a beam selection means, and a rear two-dimensional x-ray detector, where subject is located between the x-ray source and the front detector. The x-ray source emits x-rays of a single-energy spectrum for passage through the subject, where the x-rays include primary x-rays having their direction of travel unaltered by interaction with the subject, and scatter x-rays having their direction of travel altered by interaction with the subject. The front detector receives both the primary and scatter x-rays. The beam selection means permits the rear detector to receive a passed portion of the x-rays and prevents the rear detector from receiving a blocked portion of the x-rays. The rear detector receives substantially only the passed x-rays. A computer or other means is used to determine a rear low-resolution primary x-ray image at the rear detector from an image of the passed x-rays, calculate a front low-resolution primary x-ray image from the rear low-resolution primary x-ray image, calculate a front low-resolution scatter x-ray image from the front low-resolution primary x-ray image, calculate a front high-resolution scatter x-ray image from the front low-resolution scatter x-ray image, and calculate a front high-resolution primary x-ray image from the front high-resolution scatter x-ray image. Generally, the term 'resolution' can be used to describe either the image spatial resolution or the signal amplitude resolution for single pixels. In the present invention, 'resolution' is used only for image spatial resolution.

Both method embodiments include the steps of illuminating the subject with x-rays from the x-ray source, producing a low-resolution primary x-ray image at the rear detector, calculating a low-resolution primary image at the front detector, reading a high-resolution image from the front detector, producing a low-resolution image at the front detector from the front high-resolution image, subtracting the front low-resolution primary image from the front low-resolution image to determine the front low-resolution scatter image, smoothing the low-resolution scatter image by removing the high-spatial-frequency components, calculating a high-resolution scatter image by interpolation of the smoothed low-resolution scatter image, and subtracting the high-resolution scatter image from the high-resolution image to yield the high-resolution primary x-ray image at the front detector.

Other objects of the present invention will become apparent in light of the following drawings and detailed description of the invention.

BRIEF DESCRIPTION OF THE DRAWINGS

For a fuller understanding of the nature and object of the present invention, reference is made to the accompanying drawings, wherein.

DETAILED DESCRIPTION

Introduction

The present invention comprises an apparatus and method for obtaining two-dimensional x-ray images with scatter interference approximately removed. There are two preferred embodiments. Both apparatus embodiments include a single-energy spectrum x-ray source, a two-dimensional front detector, a beam selector, and a two-dimensional rear detector. In general, the beam selector passes some of the x-rays to the rear detector and blocks other x-rays from the rear detector. The difference between the apparatus embodiments is in which x-rays the beam selector passes and blocks. In the first embodiment, the beam selector passes only primary x-rays to the rear detector and blocks scatter x-rays. In the second embodiment, the beam selector passes scatter only to some locations of the rear detector, blocking primary x-rays to those locations, and passes both primary x-rays and scatter to the remainder of the locations of the rear detector.

Both method embodiments include the steps of (a) illuminating the subject with x-rays from the x-ray source, (b) producing a low-resolution primary x-ray image at the rear detector $D_{rPl}$, (c) calculating a low-resolution primary image $D_{fPl}$ at the front detector along the selected projection lines, (d) producing a high-resolution image $D_{fh}$ from the front detector, (e) producing a low-resolution image at the front detector $D_{fl}$ from $D_{fh}$, (f) subtracting $D_{fPl}$ from $D_{fl}$ to determine the low-resolution scatter component $D_{fSl}$, (g) smoothing the low-resolution scatter component $D_{fSl}$ by removing the high-spatial-frequency components, (h) calculating a high-resolution scatter image $D_{fSh}$ by interpolation of the smoothed low-resolution scatter component $D_{fSl}$, and (i) subtracting the high-resolution scatter image $D_{fSh}$ from the high-resolution image $D_{fh}$ to yield the high-resolution primary x-ray image $D_{fPh}$.

The difference between the two embodiments is the means by which the low-resolution primary image at the rear detector $D_{rPl}$ is produced.

First Embodiment

Figure 1:
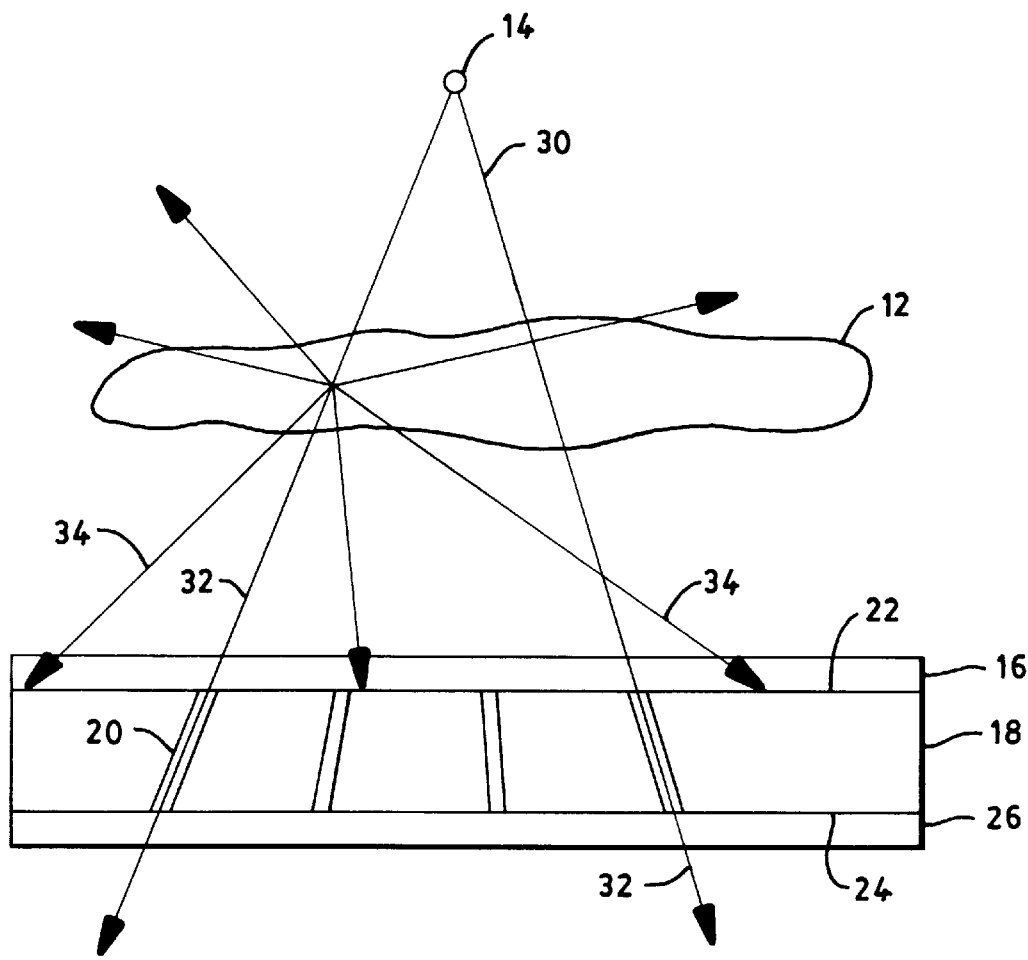
FIG. 1 illustrates the hardware of the first embodiment.

As shown in FIG. 1, the imaging system comprises an x-ray source 14, a two-dimensional front detector 16, a beam selector 18, and a two-dimensional rear detector 26. The subject under examination 12 is located between the x-ray source 14 and the front detector 16. The details of the apparatus for this embodiment are found in U.S. Pat. Nos. 5,648,997 and 5,771,269, incorporated herein by reference. There are several differences between the disclose of the '997 and '269 patents and the present embodiment. The first is that the x-ray source of the patents emits x-rays of two different energy spectrums, whereas in the present invention, the x-ray source 14 emits x-rays of only a single-energy spectrum. The second difference is that, in several embodiments of the '997 and '269 patents, the x-ray detectors are capable of distinguishing different x-ray energy levels, whereas in the present invention, this capability is not necessary.

In summary, the x-ray source 14 emits x-rays 30 of a single-energy spectrum. For simplicity in the ensuing calculations, the x-ray source 14 is assumed to be a point source. However, the present invention holds equally true when the x-ray source has a finite size. The portion the passes through the subject 12 without a change in their direction of propagation are the primary x-rays 32, and convey true information about the subject 12. The remainder of the x-rays 34 are randomly scattered as a result of interaction with the material of the subject 12. These x-rays 34 are called scatter and cause a distortion of the true information.

Both the primary x-rays 32 and scatter 34 impinge on the front detector 16. The combination of signals from all of the cells conveys an image of the x-ray intensity over the area of the front detector 16. Because the detector cells cannot distinguish between primary x-rays 32 and scatter 34, the front detector 16 conveys an image that is a combination of the primary x-rays 32 and the scatter 34, and is denoted by $$D_{fh}(x,y)=D_{fPh}(x,y)+D_{fSh}(x,y) \tag{1}$$

where the subscript lower-case f denotes the front detector 16, subscript upper-case P denotes primary x-rays 32, subscript upper-case S denotes scatter 34, subscript lower-case h denotes high-resolution, and (x,y) denotes the two-dimensional Cartesian coordinates of a cell of the front detector 16. Thus, $D_{fh}(x,y)$ denotes a high-resolution image on the front detector 16, $D_{fPh}(x,y)$ denotes the contribution from the primary x-rays 32, and $D_{fSh}(x,y)$ denotes the contribution from the scatter 34.

The present invention uses a beam selector 18 for physically separating primary x-rays from scatter. There are two types of beam selectors: type I and type II. In the first embodiment, type I beam selector is used. The type I beam selector blocks substantially the passage of all scatter 34 to the x-ray-sensitive medium of the rear detector 26, and permitting the passage of the primary x-rays 32 to those locations. In summary, the beam selector 18 must ensure that the vast majority of scatter 34 is absorbed and that, except for the primary x-rays passing through the holes 20, no other radiation, including scatter and secondary emissions caused either by primary x-rays or by scatter, reaches the rear detector 26.

After exiting the beam selector 18, the x-rays strike the rear detector assembly 26. Because of the action of the beam selector 18, the image recorded by the rear detector assembly 26 is only that of primary x-rays 32.

The term "selected location" is defined as a location on the x-ray sensitive medium of the rear detector 26 where, due to the function of the beam selector, only primary x-rays are received, and from which the scatter x-rays are substantially blocked. The "selected projection line" is defined as a straight line connecting the x-ray source 12 to a point in the "selected location". Typically, the point is close to the center of the selected location. Note that for the rear detector assembly 26 of this embodiment, only the signals at the selected locations are utilized. The rear detector cells at the selected locations have a fixed geometric relation with some of the front detector cells. This relation is established by drawing a selected projection line from the x-ray source 14 through the beam selector 18 to the selected location. This selected projection line intersects the rear detector surface at a rear detector cell at a coordinate (i,j), and intersects the front detector surface at a front detector cell at a coordinate (x(i),y(j)). Here (x(i),y(j)) denote the Cartesian coordinate (x,y) of the front detector cell in the front detector assembly 16 closest to the selected projection line. An image file $D_{rl}(i,j)$ acquired from the rear detector assembly 26 contains only the signals at the selected locations where the primary x-rays are received, and the scatter x-rays are substantially blocked. The data at the image pixel (i,j) is the data obtained either from a single detector cell or from a combination of a small number of detector cells around the selected projection line. Similarly, $D_{fl}(x(i),y(j))$ denotes an image file from the front detector assembly 26 having a low spatial resolution. The data at the image pixel (x(i),y(j)) is the data either of a single detector cell or of a combination of a small number of detector cells around the selected projection line. The relationship between (i,j) and (x(i),y(j)) is experimentally established for all of the holes 20 of the beam selector 18 and stored.

Figure 2:
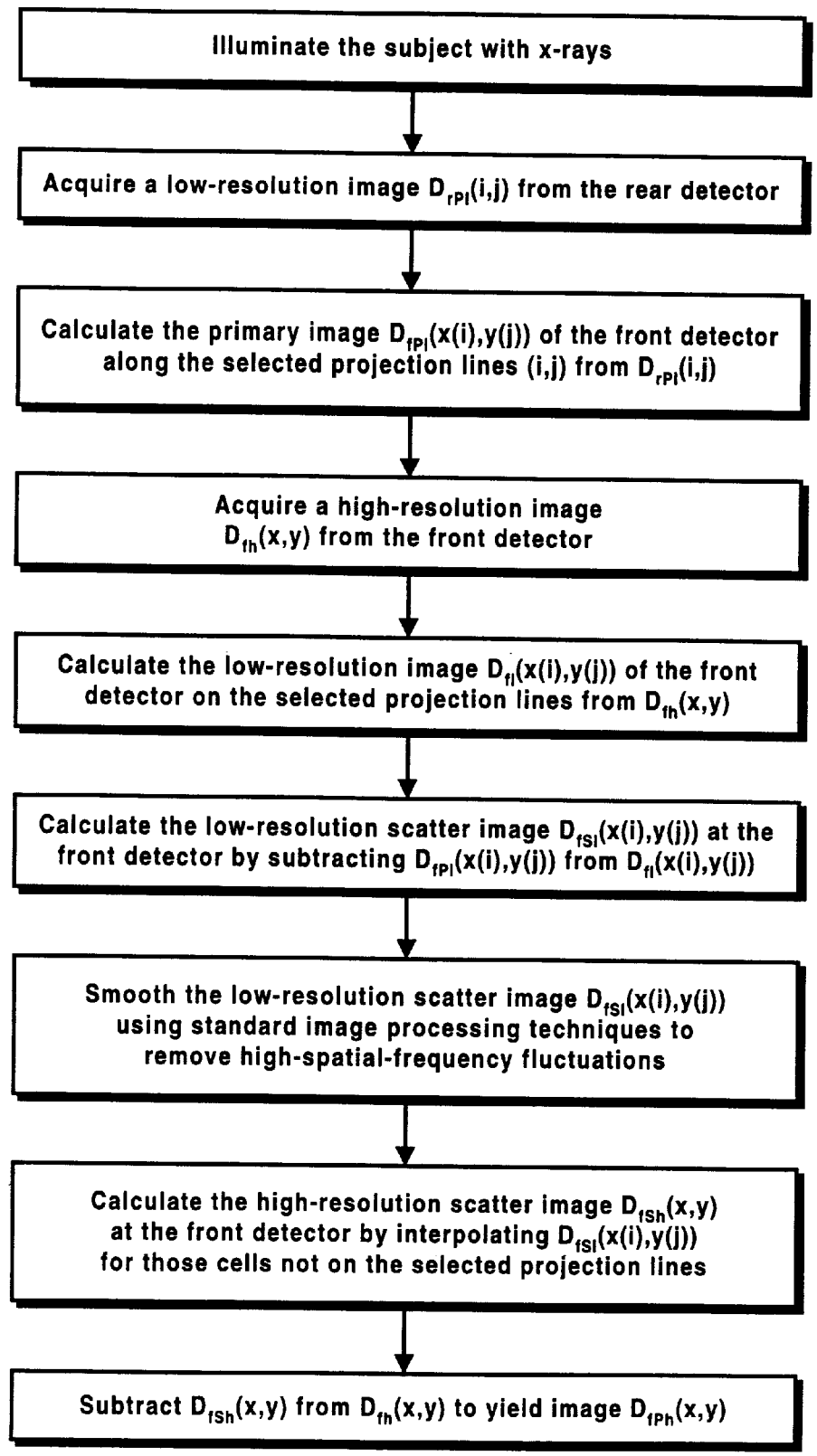
FIG. 2 is a flow diagram of the method of the first embodiment.

The method of the first embodiment for eliminating scatter is shown in the flow diagram of FIG. 2. The first step is to illuminate the subject with x-rays from the x-ray source 14. Next, a low-resolution image $I_{rl}(i,j)$ is acquired from the rear detector assembly and processed to normalize and to subtract dark signals, yielding a low-resolution image $D_{rl}(i,j)$ that is a function of the subject materials. In the present specification, "acquiring an image" is defined as transferring, via electronic means, the electrical signals induced by the x-ray illumination on each detector cell from a detector array to computer memory. Note that because of the function of the beam selector, the image of the rear detector array at the selected locations is a primary x-ray image essentially free of scatter. That is, $D_{rl}(i,j)=D_{rPl}(i,j)$.

Next, the primary image $D_{fPl}(x(i),y(j))$ of the front detector along the selected projection lines (i,j) is calculated from $D_{rPl}(i,j)$, as explained below. Then, a high-resolution image $I_{fh}(x,y)$ is acquired from the front detector and processed to normalize and to subtract dark signals, yielding a high-resolution image $D_{fh}(x,y)$, which is the sum of primary x-rays and scatter x-rays. Next, the low-resolution image of the front detector $D_{fl}(x(i),y(j))$ at the detector cells on the selected projection lines is calculated from $D_{fh}(x,y)$. Then, $D_{fPl}(x(i),y(j))$ is subtracted from $D_{fl}(x(i),y(j))$ to determine the low-resolution scatter component $D_{fSl}(x(i),y(j))$ of the image $D_{fh}(x(i),y(j))$ at the detector cells on selected projection lines.

Next, standard image processing procedures are used to smooth the low-resolution scatter image $D_{fSl}(x,y)$ by removing the high-spatial-frequency fluctuations in the scatter image and to ensure only the low-spatial-frequency signals that is consistent with the nature of scatter can exist in the image. According to Compton scatter theory and experimental data, the image produced by the scatter on a two-dimensional x-ray detector is quite smooth, or put another way, has only a relatively low spatial frequency. On the other hand, by using the single energy method, the relationship between the primary image of the front detector $D_{fPl}(x(i),y(j))$ and the primary image of the rear detector $D_{rPl}(i,j)$ can only be established approximately. There is always a slight deviation between the calculated primary front detector x-ray image and the true primary image of the front detector. The difference between the true primary x-ray image and the calculated primary x-ray image is an image with a spatial frequency much higher than that due to scatter. Thus, even though the exact deviation in the primary image is not known, by removing the high-frequency component from the calculated scatter image, the accuracy of the approximation can be significantly improved.

Next, the smoothed $D_{fSl}(x(i),y(j))$ image is interpolated for those front detector cells not on the selected projection lines, yielding the high-resolution scatter image $D_{fSh}(x,y)$.

Finally, the image $D_{fSh}(x,y)$ is subtracted from $D_{fh}(x,y)$ to yield an image $D_{fPh}(x,y)$, which is a full two-dimensional image of the subject at the front detector after scatter x-rays have been substantially eliminated.

The following presents the method for calculating the primary image $D_{fPl}(x(i),y(j))$ of the front detector from the primary image $D_{rPl}(i,j)$ of the rear detector. Note that the major challenge comes from the fact that the x-rays have a distributed energy spectrum. Because of this, the relationship between the signals of the front detector and the signals of the rear detector is generally dependent on the specific x-ray energy spectrum, or equivalently dependent on the image subject which changes from case to case, and from pixel to pixel. In U.S. Pat. Nos. 5,648,997 and 5,771,269, it is shown that by using a dual-energy method, an accurate relationship can be rigorously established without making assumptions about the nature of the apparatus or subject. The present invention provides an approximation method for establishing a reasonably accurate relationship between the front detector low-resolution primary image and the rear detector low-resolution primary image without using dual energy. In terms of establishing a front-rear primary signal relationship, the most important aspects of the present invention are summarized below.

(A) When the image subject has only one type of tissue with a single attenuation coefficient $\mu_a(E)$, an accurate relationship between the primary image of the front detector and the primary image of the rear detector can be established. Such a relationship is independent of image subject and holds universally true on a pixel-on-pixel basis. A mathematical showing of this conclusion is described below.

(B) Based on (A) above, if the image subject is an organ composed only of soft tissue, an approximate front-rear relationship can also be established with reasonable accuracy. The reason is that the mass attenuation coefficients of the components of the soft tissue, the fat tissue and the lean tissue, are very similar. A single average tissue composition can be used to replace fat and lean tissue. The present invention provides a method for correction of the deviation from the average tissue value, and is described below. This method is especially suitable for mammography.

(C) When bone is present, if the bone volume is not too large, the effect of bone on scatter distribution can also be corrected with a reasonably good accuracy.

These three aspects are now described in more detail:

(A) When the image subject has only a single material composition with an x-ray attenuation coefficient function $\mu_a(E)$, the primary x-ray signal for the rear low-resolution detector (i,j) can be written as $$D_{rPl}(i,j) = \int [\Phi_0(E) \exp(-(\mu_a(E) \times t_a(i,j)) \times S_r(E)] dE \qquad (2)$$

and the primary x-ray low-resolution image of the front detector 16 can be written as $$D_{fPl}(x(i),y(j)) = \int [\Phi_0(E) \exp(-(\mu_a(E) \times t_a(x(i),y(j))] \times S_f(E) dE \qquad (3)$$

where $\Phi_0(E)$ is the energy spectra of the x-ray source 14. The average projection mass density $t_a(x,y)$ of the subject 12 is in units of grams/centimeters$^2$ (g/cM$^2$). The mass attenuation coefficient $\mu_a(E)$ is expressed in units of centimeter$^2$/gram (cm$^2$/g). $S_f(E)$ is the x-ray spectral sensitivity (the electrical signal amplitude from the detector as a function of the number of x-rays with energy E after the x-rays passing through the image subject and the passing through the front detector) of the front detector. $S_r(E)$ is the x-ray spectral sensitivity of the rear detector, and includes not only the x-ray spectral sensitivity of the detector itself, but also the x-ray transmission factor that accounts for the absorption of x-rays due to the subject 12 and due to the front detector 16.

Equations (2) and (3) constitute a nonlinear equation system. Generally, it is too complicated to predict whether a nonlinear equation system is solvable or not. However, in the present case, it can be shown mathematically that for any measured value of the signal $D_{rPf}(i,j)$ within a reasonable range, equation (2) always has a unique solution for the tissue projection density value $t_a(i,j)$. This comes from the fact that equation (2) is a monotonically decreasing function of $t_a(i,j)$. This means that $D_{rPf}(i,j)$ and $t_a(i,j)$ have a rigorous one-to-one correspondence. The same is true for equation (3) between the signal $D_{fPf}(x(i),y(j))$ and $t_a(i,j)$. Therefore, the primary x-ray image signal $D_{fPf}(x(i),y(j))$ and the primary x-ray image signal $D_{rPf}(i,j)$ have a one-to-one correspondence relationship. This relationship is true for any image subject (for any value of the tissue density $t_a(i,j)$), and is universally true for all pixels on a pixel-by-pixel basis.

Because the relationship is independent of the image subject, the exact relationship can be established through calibration, that is, measurements in absence of the image subject. The following is a brief description of the calibration procedures. A number of plates with an average attenuation coefficient $\mu_a(E)$ and known integrated area density $t_a[n]$, where [n] represents a plate having a discrete plate thickness ranging from 0 up to the maximum tissue thickness of a human organ in question, are inserted one at a time in place of the subject. The primary x-ray signal of a typical normalized detector cell of the front detector $D_{fP}$ is measured and the primary x-ray signal of a typical detector cell of the rear detector $D_{RP}$ is measured, all under otherwise the same conditions. As a result, two numerical relationships are established as $$D_{fP}=f(t_a[n])\qquad(4)$$

$$D_{rP}=g(t_a[n])\qquad(5)$$

Equations (4) and (5) have only a small number of discrete values. Typically the maximum calibration value has from 10 steps to 100 steps of $t_a[n]$, (n=1, 2, 3 . . . , 100). However, it is known that both equations (2) and (3) are continuous and smooth functions. Thus, it is legitimate to obtain the entire functional relationship through interpolation without losing accuracy. After interpolation, equation (4) and (5) each becomes practically continuous, each having tens of thousands values with very small steps of $\delta t_a$. So, after interpolation, two practically continuous smooth functions are obtained as $$D_{fP}=F(t_a)\qquad(6)$$

$$D_{rP}=G(t_a)\qquad(7)$$

It is known that each of these equations are monotonic in terms of $t_a$, and the solution is unique. So by numerical inversion, or reordering, a unique relationship between the front primary x-ray signal $D_{fP}$ and the rear primary x-ray signal is obtained.

$$D_{fP}=Q(D_{rP})\qquad(8)$$

Thus, it is shown that for a typical normalized detector cell, there is a well-defined one-to-one relationship between the primary x-ray signal of the front detector and the primary x-ray signal of the rear detector. The method for obtaining the numerical relationship has also been described.

When medical x-ray imaging is performed, generally the primary x-ray signal of the front detector cannot be directly measured, but the primary x-ray signal of the rear detector can be directly measured according to the hardware configuration as described above by using a beam selector. According to the directly measured primary x-ray signal $D_{rP}$, by using the calibration curve of equation (8), the primary x-ray signal $D_{fP}$ can be calculated on pixel-by-pixel basis.

When the primary x-ray image component $D_{fPf}(x(i),y(j))$ is calculated on pixel-by-pixel basis, a low-spatial-resolution scatter image of the front detector can be calculated by subtraction, as so $$D_{fSf}(x(i),y(j))=D_{fl}(x(i),y(j))-D_{fPf}(x(i),y(j))\qquad(9)$$

The next step is to interpolate the low-resolution scatter image to all pixels of the front detector as $D_{fSh}$. This is legitimate and accurate, because Compton scattering has a rather smooth angular distribution, as has been shown experimentally. The interpolated high-resolution scatter image $D_{fSh}(x,y)$ is subtracted from the measured front detector image $D_{fh}(x,y)$ to obtain the high-resolution primary image free of scatter $$D_{fPh}(x,y)=D_{fh}(x,y)-D_{fSh}(x,y)\qquad(10)$$

Note that even though there are a large number of arithmetic operations, these operations do not cause much increase in error and noise, because these operations are conducted on smoothly changing scatter images.

(B) When the image subject is composed of soft tissue only, an average tissue can be used for establishing the front-rear primary x-ray signal relationship. The mass attenuation coefficient of such an average tissue is written as $$\mu_a(E)=P_u\times\mu_u(E)+P_v\times\mu_v(E)\qquad(11)$$

where $P_u$ and $P_v$ are the percentages of fat tissue and lean tissue, respectively. Accuracy can be further improved by making corrections to the high-frequency and medium-frequency fluctuations in scatter images.

After the low-resolution scatter image $D_{fSf}(x(i),y(j))$ is calculated, it is often found that if the image data is plotted in a three-dimensional space, with the signal intensity as a function of (x(i), y(j)), the trend of signal intensity changes can be grossly divided into three frequency components. The slowly changing trend, which is called the low-spatial-frequency component, is attributed to the true scatter signals. There are also some high-frequency and some medium-frequency fluctuations superimposed on the scatter image data. These fluctuations are small, caused by imperfections of the approximations. A high-frequency fluctuation is defined as a significant signal change between, for example, two to three pixels in the low-resolution image. A medium-frequency fluctuation is defined as a significant signal change between, for example, five to ten pixels. If the total pixel number is approximately 100×100, the true scatter image should have a slow change over more than ten pixels. The division of high, medium, and low frequency is only relative and very much dependent on experimental conditions, especially on the image subject and the spatial resolution of the low resolution detectors. Low-frequency components should correspond to true scatter image data, because the spatial frequency is consistent with that estimated by standard Compton scattering calculations. Medium-frequency change is caused by the deviation of the actual tissue composition in a broad region from the average tissue composition $t_a$ used in calculations. High-frequency change is caused by more localized deviation of the tissue composition from the average tissue composition $t_a$ used in calculations. The reason for the division of the fluctuation errors into medium-frequency and high-frequency components is that different correction methods are used.

For the correction of the medium-frequency fluctuations, the average mass attenuation coefficient of equation (11) is systematically changed, and through comparison, an optimal value $P_u$ is chosen. First, assume a percentage composition $P_u$ and $P_v=100\%-P_u$. Then use the above-described procedures to calculate a low-resolution scatter image $D_{fsf}(x(i),y(j))$. Repeat this procedure a number of times, changing $P_u$ to a number of step values, for example, $P_u=10\%, 20\%, \ldots, 50\%, \ldots, 100\%$, using each step value $P_u$ to make the same calculations and to calculate and to plot all the corresponding low-resolution scatter images $D_{fsf}(x(i),y(j))$. After the calculations, compare the images to choose the one with the least medium-frequency fluctuations. This specific value of $P_u$ should represent the closest approximation for the tissue composition in the subject region under consideration. The whole image subject may use a single approximate $P_u$, or the image subject can be divided into a number of subregions, where each subregion has its own $P_u$ value. For example, in the case of breast imaging, the simplest option is to divide the whole breast into a fat-tissue-dominant subregion and lean-tissue-dominant subregion. First, draw an approximate closed curve for the lean-tissue-dominant subregion according to the organ structure. Typically, the fat-tissue-dominant subregion is outside the lean-tissue-dominant subregion. Using a number of $P_u$ values for each subregion, choose the best $P_u$ value for each subregion separately. Alternatively, transitional subregions between the two dominant subregions are defined and separate $P_u$ values are calculated for these subregions to obtain gradually changing values for $P_u$.

(C) In the case of bone imaging, the whole image can be divided into a soft tissue region and a bone region. A standard average soft tissue composition value can be used as a good approximation for the entire soft tissue region without the need to further differentiate fat tissue and lean tissue. The bone region can be automatically detected by using standard x-ray software packages. Inside the bone image, one or more than one subregion can be encircled, each having an average chemical composition $$\mu_a(E)=P_t\times\mu_t(E)+P_b\times\mu_b(E) \qquad (12)$$

where $P_t+P_t=100\%$, $\mu_t$ is the standard soft tissue attenuation coefficient, and $\mu_b(E)$ is the standard bone attenuation coefficient. A number of step values $P_t=10\%, 20\%, \ldots, 100\%$ are chosen and the corresponding low-resolution scatter image $D_{fsf}(x(i),y(j))$ is calculated for each value. Then all the $D_{fsf}(x(i),y(j))$ images are plotted separately in three-dimensional space, and, through comparison, an optimal value $P_t$ for the specific subregion under consideration is chosen. These procedures appear laborious. But with appropriate calibration data, a single computer software package can process all the steps, so that the correction of medium-frequency fluctuations can be carried out automatically and quickly.

Correction for the high-frequency fluctuations can be carried out by using standard curve-smoothing algorithms.

Note that in both the medium-frequency and the high-frequency corrections, there are some tasks and results that depend on the operator's judgment. This is inevitable, because, due to its nature, the single-energy method cannot provide a complete set of data for uniquely determining the scatter image. However, the medium-frequency and high-frequency components are all very small in comparison with the true scatter signals, so the deviation from one operator to another operator will also be small.

Second Embodiment

Figure 3:
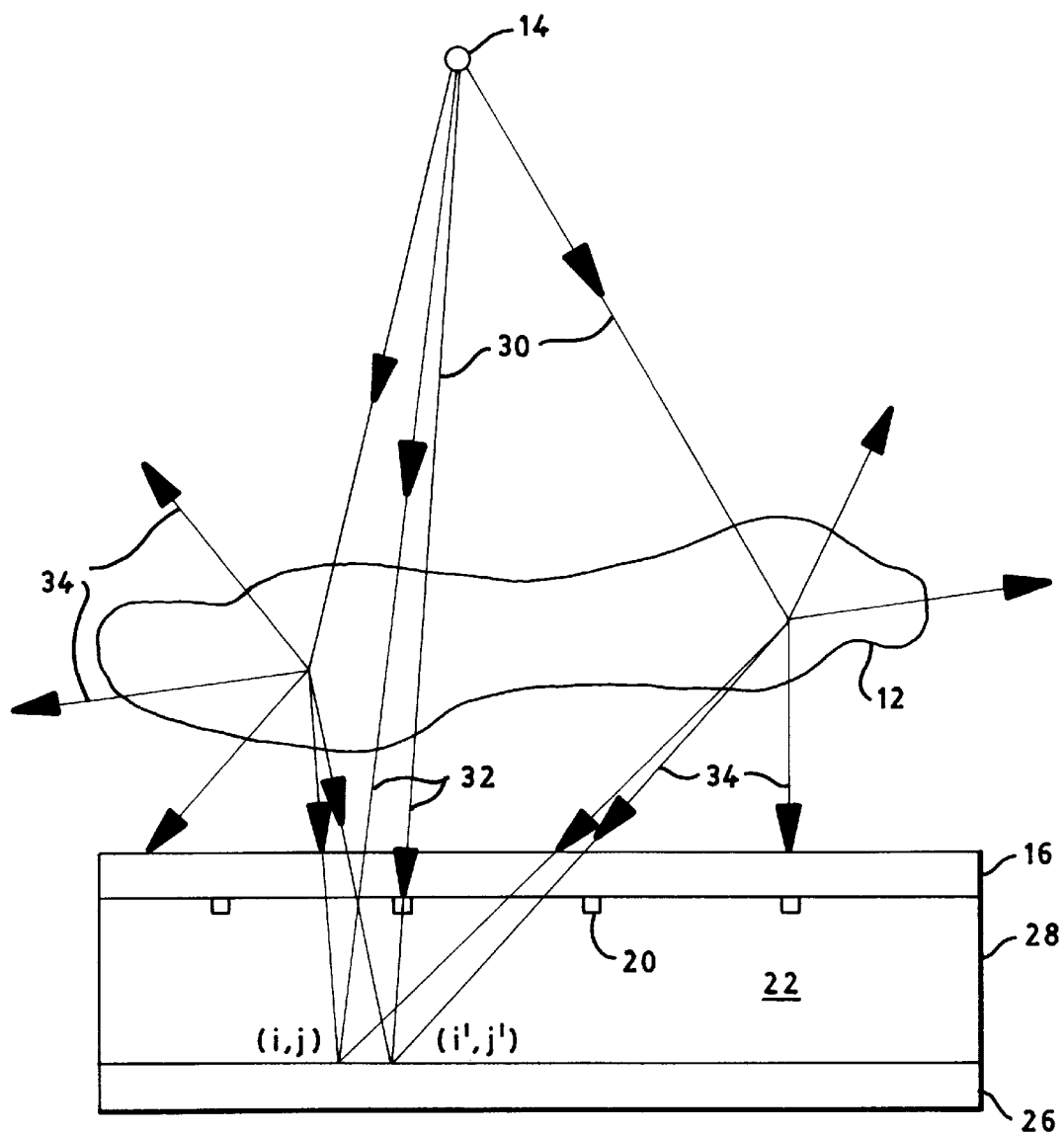
FIG. 3 illustrates the hardware of the second embodiment.

In the second embodiment of the apparatus, shown in FIG. 3, the beam selector 28 is a type II, rather than a type I. The type II beam selector substantially blocks the passage of all primary x-rays 32 from the image subject 12 to a number of shadowed locations on the x-ray-sensitive medium of the rear detector assembly 26, permitting the passage of only scatter 34 to those shadowed locations.

The entire imaging system is essentially the same as that described in U.S. patent application Ser. No. 09/025,926, incorporated herein by reference. There are several differences between the disclosure of the '926 application and the present embodiment. The first is that the x-ray source of the patents emits x-rays of two different energy spectrums, whereas in the present invention, the x-ray source 14 emits x-rays of only a single-energy spectrum. The second difference is that the x-ray detectors in the '926 application are capable of distinguishing different x-ray energy levels, whereas in the present invention, this capability is not necessary.

There are two images received by the rear detector 26. The first includes only of scatter signals 34 at the shadowed locations, which are denoted as (i',j'). The second image includes a combination of primary x-rays 32 and scatter 34 at the non-shadowed locations, which are denoted as (i,j). In the present invention, these two images are used to derive a low-resolution primary x-ray image data at the rear detector at selected locations. The term "selected location" is defined as the locations on the rear detector 28, where, due to the function of the beam selector 18 and to the use of the procedures of the present invention, the signals contain only derived primary x-rays. This definition of "selected location" ensures consistency between the present embodiment and the first embodiment.

The rear detector cells at the selected locations have a fixed geometric relation with some of the front detector cells. This relation is established by drawing a selected projection line from the x-ray source 14 through the beam selector 18 to the selected location. As shown in FIG. 3, this selected projection line intersects the rear detector surface at a rear detector cell at a coordinate (i,j), and intersects the front detector surface at a front detector cell at a coordinate (x(i),y(j)). An image file $D_{rf}(i,j)$ at the selected locations is a low-resolution image file, and $D_{fl}(x(i),y(j))$ denotes an image file from the front detector having a low spatial resolution. The relationship between (i,j) and (x(i),y(j)) is experimentally established and stored.

Figure 4:
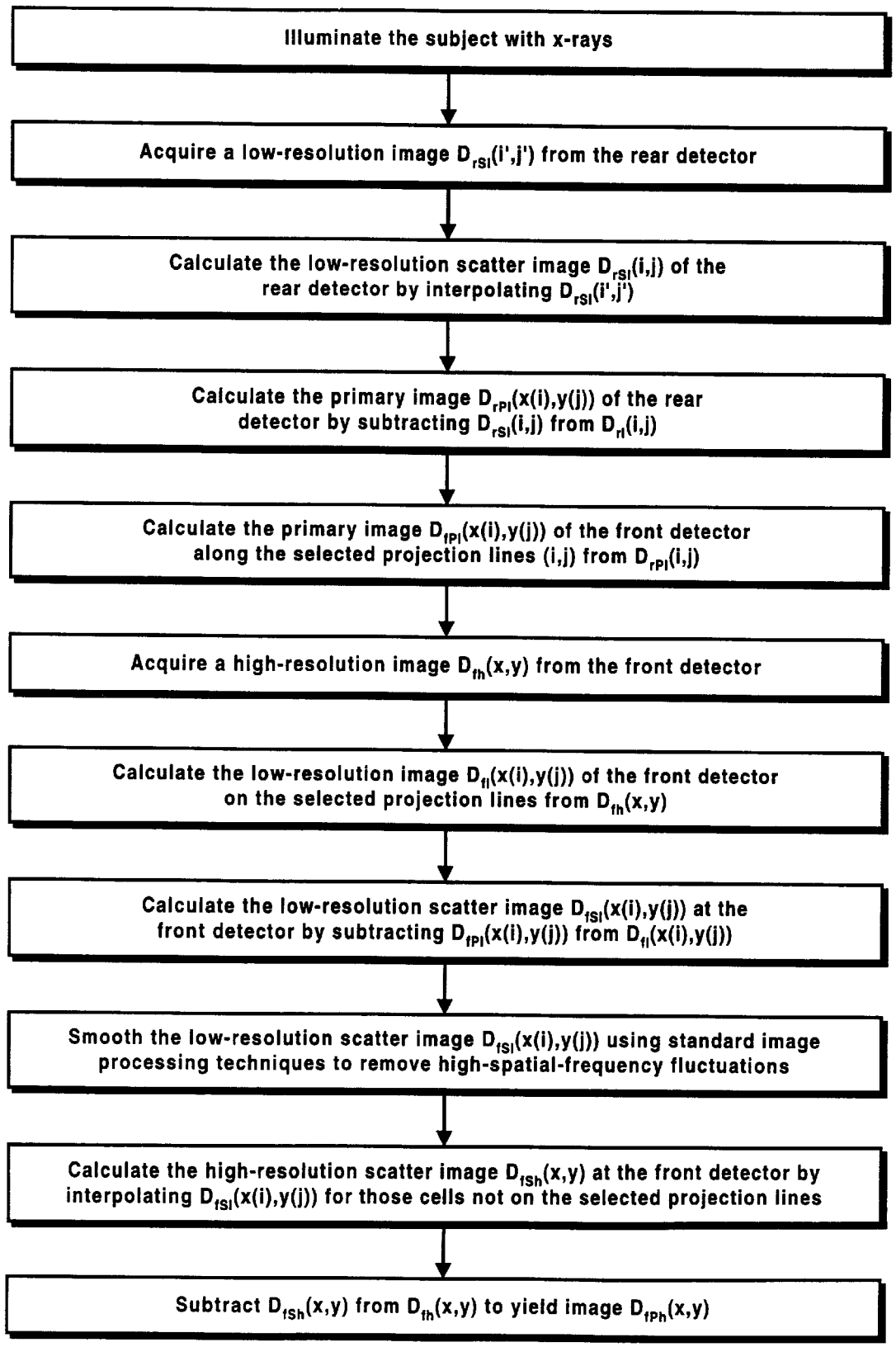
FIG. 4 is a flow diagram of the method of the second embodiment.

The method of the second embodiment is shown in the flow diagram of FIG. 4. Two images of the rear detector are acquired. The coordinates in each of these two images have a general notation (I,J), with I=1, 2, 3, ..., N and J=1, 2, 3, ..., M, where M and N are integers. (I,J) has two subsets, (i,j) and (i',j'). The data subset at (i',j') includes the scatter-only x-rays, and is identified as $D_{rSf}(i',j')$. The data subset at (i,j) includes a combination of primary x-rays and scatter, and is identified as $D_{rf}(i,j)$. The locations (i,j) are selected to uniformly cover the entire image plane of the rear detector and close to the locations (i',j'). Because image $D_{rSt}(i',j')$ is from scatter-only x-ray signals, they can be extended to the entire image plane of the rear detector by interpolation. The interpolation does not cause significant error because of the physical nature of the scatter x-rays. As long as there are a sufficiently large number of data points, the error incurred due to interpolation is negligible in comparison with other error sources, such as statistical fluctuations of x-ray photon numbers. So, scatter-only signals at the selected location (i,j) are obtained by interpolation, and identified as $D_{rSt}(i,j)$. Accordingly, a primary image signals $D_{rPt}(i,j)$ can be calculated as $$D_{rPt}(i,j)=D_{rt}(i,j)-D_{rSt}(i,j) \qquad (13)$$

where $D_{rt}(i,j)$ is the directly acquired data and $D_{rSt}(i,j)$ is the interpolated data.

Once the low-resolution primary image at the rear detector is determined, the remainder of the method to determine the high-resolution primary x-ray image of the subject is the same as that of the first embodiment.

A beam stop method to reduce scatter effects is disclosed in the article Lo, Floyd et al., *Scatter Compensation in Digital Chest Radiography Using the Posterior Beam Stop Technique,* 21 Medical Physics 435 (March, 1994). Lo, Floyd uses a beam stop array sandwiched between two stimulated phosphor screens to acquire a scatter-only image at the rear screen. Then a scatter image at the front detector is obtained by multiplying the rear scatter image by a constant. There is certain similarity in the gross geometry to the present invention, but the similarity is only superficial. There are several essential differences between the present invention and the method of Lo, Floyd. The first is that the key part of the method of Lo, Floyd is in trying to establish a relationship of scatter images on the front detector and the scatter image on the rear detector, while a key aspect of the method of the present invention is to establish the relationship between the primary images of the front detector and the primary image of the rear detector. A sound theoretical foundation for the method of Lo, Floyd has yet to be found. It should be noted that, according to generally accepted theory, scatter x-ray photons have rather complex and rather broad unknown spatial distributions, and at the same time have rather complex and rather broad unknown energy distributions, the factors affecting the scatter signals are too complicated to be tractable. So far, there has been no evidence that this generally accepted concept should be rejected.

Secondly, because of the differences in the theory and in the method between Floyd and the present invention, the hardware also has essential differences. The most important specific difference in the hardware is that, Lo, Floyd's method only requires that the detector cells behind the beam stop can detect a pure scatter signal. There are no further requirements. Specifically, there is no requirement regarding those detector cells that are not blocked by the beam stop. Whether those unblocked detector cells can detect a zero signal or whether they are simply not functional and not able to detect anything, is irrelevant for Lo, Floyd's method. In a word, Lo, Floyd's method only requires detection of one image, a scatter image. On the other hand, the method of the present invention requires that two mutually exclusive images must be recorded by the low-resolution rear detector array, the scatter image from those detector cells behind the absorption cylinder blocks and the combination primary x-ray/scatter image from the detector cells not blocked by the absorption blocks. It is required by the present invention that unblocked detector cells record a composite signal containing accurate data both for the primary x-rays and accurate data for the scatter, and that the position of the unblocked detector cells must be sufficiently close to the blocked detector cells. The primary x-ray image at the selected detection locations (i,j) must not be distorted. The distortion is defined as irregular obstruction of the primary x-rays transmission along their projection lines (i,j). When there is no x-ray absorbent substance present on the x-ray path, there is no distortion. When there is some substance present on the x-ray path, the x-ray transmission must be accurately known. Otherwise, the relationship between the primary signal of the front detector and the primary signal of the rear detector at the location (i,j) cannot be established. On the other hand, Lo, Floyd's system excludes any requirements regarding the primary x-rays at all. Consequently, these important requirements for the present invention are irrelevant for Lo, Floyd's system.

Finally, Lo, Floyd's detector is a stimulated phosphor plate which is only a semiquantative device, and is not suitable for high accuracy quantitative imaging. The digital detectors required by the present invention are highly-accurate, quantitative, large format, integrated semiconductor detector arrays.

The foregoing descriptions of the preferred embodiments of the invention have been presented for the purpose of illustration and description. They are not intended to be exhaustive or to limit the invention to the precise form disclosed. Many modifications and variations are possible in light of the above teaching. It is intended that the scope of the invention be limited not by this detailed description, but rather by the claims appended hereto.

Thus it has been shown and described an apparatus and method for removing scatter from an x-ray image using a single-energy x-ray source and a two-dimensional detector which satisfies the objects set forth above.

Since certain changes may be made in the present disclosure without departing from the scope of the present invention, it is intended that all matter described in the foregoing specification and shown in the accompanying drawings be interpreted as illustrative and not in a limiting sense.

What is claimed is:

1. A two-dimensional x-ray imaging system for taking images of a subject, said system comprising:

(a) in physical sequence from front to back, an x-ray source, a front two-dimensional x-ray detector, a beam selection means, and a rear two-dimensional x-ray detector, said subject being located between said x-ray source and said front detector;

(b) said x-ray source being adapted to emit x-rays of a single-energy spectrum for passage through said subject, said x-rays including primary x-rays having their direction of travel unaltered by interaction with said subject and said x-rays including scatter x-rays having their direction of travel altered by interaction with said subject;

(c) said front detector receiving said primary x-rays and said scatter x-rays, said front detector being incapable of distinguishing different x-ray energy levels;

(d) said beam selection means permitting said rear detector to receive a passed portion of said x-rays and preventing said rear detector from receiving a blocked portion of said x-rays;

(e) said rear detector receiving substantially only said passed x-rays, said rear detector being incapable of distinguishing different x-ray energy levels; and (f) a computing means for determining a rear low-resolution primary x-ray image at said rear detector from an image of said passed x-rays, calculating a front low-resolution primary x-ray image from said rear low-resolution primary x-ray image, calculating a front low-resolution scatter x-ray image from said front low-resolution primary x-ray image, calculating a front high-resolution scatter x-ray image from said front low-resolution scatter x-ray image, and calculating a front high-resolution primary x-ray image from said front high-resolution scatter x-ray image.

2. The x-ray imaging system of claim 1 wherein said beam selection means permits rear selected detection locations of said rear detector to receive said primary x-rays and substantially prevents said rear selected detection locations from receiving said scatter x-rays.

3. The x-ray imaging system of claim 2 wherein said beam selection means is substantially comprised of an x-ray-absorbent material having a plurality of holes, the axes of said holes being parallel to the direction of travel of said primary x-rays.

4. The x-ray imaging system of claim 1 wherein said rear detector has a plurality of rear selected detection locations and a plurality of rear shadowed detection locations, said rear selected detection locations and said rear shadowed detection locations being mutually exclusive, and said beam selection means prevents passage of said primary x-rays to said rear shadowed detection locations, allows passage of said scatter x-rays to said rear shadowed detection locations, and allows passage of said primary x-rays and said scatter x-rays to said rear selected detection locations.

5. The x-ray imaging system of claim 4 wherein said beam selection means is substantially comprised of an x-ray-transparent material having a plurality of blocks of x-ray absorbent material, the axes of said blocks being parallel to the direction of travel of said primary x-rays.

6. The x-ray imaging system of claim 1 wherein said x-ray source is adapted to emit x-rays with an average energy in the range of from approximately 15 keV to approximately 500 keV.

7. The x-ray imaging system of claim 1 wherein said front detector includes a plurality of x-ray-sensitive detector cells arranged in a substantially rectangular matrix with from approximately 128 to approximately 16,384 detector cells on a side.

8. The x-ray imaging system of claim 1 wherein said rear detector includes a plurality of x-ray-sensitive detector cells arranged in a substantially rectangular matrix with from approximately 8 to approximately 1,024 detector cells on a side.

9. A method for taking a two-dimensional x-ray image of a subject using a two-dimensional x-ray imaging system, said imaging system including, in physical sequence from front to back, an x-ray source, a front two-dimensional x-ray detector having a plurality of front detection locations identified by a notation (x,y), said front detector being incapable of distinguishing different x-ray energy levels, a beam selection means, and a rear detector having a plurality of rear selected detection locations identified by a notation (i,j), said rear detector being incapable of distinguishing different x-ray energy levels, said subject being between said x-ray source and said front detector and having a mass attenuation coefficient function of $\mu_a(E)$, wherein E is an x-ray photon energy, said x-ray source being adapted to emit x-rays for passage through said subject, said x-rays including primary x-rays having their direction of travel unaltered by interaction with said subject and said x-rays including scatter x-rays having their direction of travel altered by interaction with said subject, said beam selection means permitting said rear detector to receive a passed portion of said x-rays and preventing said rear detector from receiving a blocked portion of said x-rays, and selected front detection locations being those of said front detection locations intersected by x-ray projection lines extending from said x-ray source to said selected rear detection locations, said selected front detection locations being identified by a notation (x(i),y(j)), said method comprising:

(a) illuminating said subject with said x-rays;

(b) determining a low-resolution image $D_{rPl}(i,j)$ composed of substantially only said primary x-rays at said selected detection locations of said rear detector;

(c) calculating a low-resolution primary x-ray image $D_{fPl}(x(i),y(j))$ at said front detector from said image $D_{rPl}(i,j)$;

(d) acquiring a high-resolution image $I_{fh}(x,y)$ from said front detection locations and processing said image $I_{fh}(x,y)$ to normalize it and to subtract dark signals, yielding an image $D_{fh}(x,y)$, which is composed of said primary x-rays and said scatter x-rays;

(e) producing, from said image $D_{fh}(x,y)$, a low-resolution image $D_{fl}(x(i),y(j))$ representing said selected front detection locations;

(f) calculating a low-resolution scatter x-ray image $D_{fSl}(x(i),y(j))$ at said front detector by subtracting said low-resolution primary x-ray image $D_{fPl}(x(i),y(j))$ from said low-resolution image $D_{fl}(x(i),y(j))$;

(g) removing high-spatial-frequency fluctuations from said low-resolution scatter x-ray image $D_{fSl}(x(i),y(j))$ to produce a smoothed low-resolution scatter x-ray image $D_{fSl}(x(i),y(j))$;

(h) calculating a high-resolution scatter x-ray image $D_{fSh}(x,y)$ by extending said smoothed low-resolution scatter x-ray image $D_{fSl}(x(i),y(j))$ to the entire image area of said front detector through interpolation; and (i) calculating a high-resolution primary x-ray image $D_{fPh}(x,y)$ by subtracting said high-resolution scatter x-ray image $D_{fSh}(x,y)$ from said high-resolution image $D_{fh}(x,y)$;

(j) whereby said high-resolution primary x-ray image $D_{fPh}(x,y)$ is a two-dimensional image of said subject at said front detector after said scatter x-rays have been substantially eliminated, said image $D_{fPh}(x,y)$ having a spatial resolution substantially equal to the highest spatial resolution available from said front detector.

10. The method for taking a two-dimensional x-ray image of claim 9 wherein said beam selection means permits said selected rear detection locations to receive said primary x-rays and prevents said selected rear detection locations from receiving substantially all of said scatter x-rays, and said production of said low-resolution image $D_{rPl}(i,j)$ at said rear detector composed of substantially only said primary x-rays includes acquiring a low-resolution primary x-ray image $I_{rPl}(i,j)$ from said selected rear detection locations and processing said image $I_{rPl}(i,j)$ to normalize it and to subtract dark signals, yielding said image $D_{rPl}(i,j)$.

11. The method for taking a two-dimensional x-ray image of claim 9 wherein said rear detector has a plurality of shadowed rear detection locations identified by the notation (i',j'), said selected rear detection locations and said shadowed rear detection locations being mutually exclusive, said beam selection means prevents passage of said primary x-rays to said shadowed rear detection locations, allows passage of said scatter x-rays to said shadowed rear detection locations, and allows passage of said primary x-rays and said scatter x-rays to said selected rear detection locations, and said production of said low-resolution image $D_{rPl}$ at said rear detector composed of substantially only said primary x-rays includes the steps of:

(a) acquiring a low-resolution image $I_{rl}(i,j)$ from said selected rear detection locations and processing said image $I_{rl}(i,j)$ to normalize it and to subtract dark signals, yielding an image $D_{rl}(i,j)$;

(b) acquiring a low-resolution scatter x-ray image $I_{rSl}(i',j')$ from said shadowed rear detection locations and processing said image $I_{rSl}(i',j')$ to normalize it and to subtract dark signals, yielding an image $D_{rSl}(i',j')$;

(c) calculating a low-resolution scatter x-ray image $D_{rSl}(i,j)$ by extending said low-resolution scatter x-ray image $D_{rSl}(i',j')$ to said selected rear detection locations through interpolation; and (d) calculating said low-resolution primary x-ray image $D_{rPl}(i,j)$ by subtracting said image $D_{rSl}(i,j)$ from said image $D_{rl}(i,j)$.

12. The method for taking a two-dimensional x-ray image of claim 9 wherein said calculation of a low-resolution primary x-ray image $D_{fPl}(x(i),y(j))$ at said front detector from said image $D_{rPl}(i,j)$ is performed by using a function $D_{fP}=Q(D_{rP})$, said function being determined by calibration.

13. The method for taking a two-dimensional x-ray image of claim 12 wherein said calibration comprises the steps of:

(a) providing a plurality of plates n, each having an average attenuation coefficient $\mu_a$ and a known integrated area density $t_a[n]$;

(b) inserting each of said plates in place of said subject and reading a primary x-ray image $D_{fP}$ at said front detector and reading a primary x-ray image $D_{rP}$ at said rear detector for each of said plates, resulting in numerical relationships $D_{fP}=f(t_a[n])$ and $D_{rP}=G(t_a[n])$;

(c) interpolating said relationships to yield the equations $D_{fP}=F(t_a)$ and $D_{rP}=G(t_a)$; and (d) solving said equations to yield said function $D_{fP}=Q(D_{rP})$.

14. The method for taking a two-dimensional x-ray image of claim 9 wherein said subject is a combination of two materials u and v, said attenuation coefficient of said subject is $\mu_a=P_u\times\mu_u+P_v\times\mu_v$, and optimal values of percentages $P_u$ and $P_v$ are determined by calculating said low-resolution scatter image $D_{fSl}(x(i),y(j))$ for predetermined values of $P_u$ and $P_v$, plotting said calculated images for each of said predetermined values of $P_u$ and $P_v$, and selecting the one of said predetermined values of said $P_u$ and $P_v$ that has a calculated images with the least medium spatial frequency.

* * * * *